United States Patent [19]

Ellman et al.

[11] 4,380,433
[45] Apr. 19, 1983

[54] DENTAL WIRE DISPENSER AND MOUNTING TOOL

[76] Inventors: Alan G. Ellman, 1 Auerbach La., Lawrence, N.Y. 11516; Jon C. Garito, 22 Deering La., East Rockaway, N.Y. 11558

[21] Appl. No.: 267,007

[22] Filed: May 26, 1981

Related U.S. Application Data

[63] Continuation of Ser. No. 61,276, Jul. 27, 1979, abandoned, which is a continuation-in-part of Ser. No. 917,533, Jun. 21, 1978, abandoned.

[51] Int. Cl.³ .......................... A61C 1/10; A61C 1/12; A61C 17/02; B25G 3/28
[52] U.S. Cl. ........................................ 433/87; 433/89; 433/225; 403/354; 403/289; 279/46 A; 226/127; 226/128
[58] Field of Search .............. 433/87, 89, 3, 225, 433/221; 226/127, 128; 221/302, 312 R; 140/123; 242/129.53, 129.62, 129.72, 125; 401/82; 403/289, 354; 428/399; 279/1.5 G, 46 A, 46 R, 96

[56] References Cited

U.S. PATENT DOCUMENTS

| 80,378 | 7/1868 | Wright | 403/354 |
|---|---|---|---|
| 161,842 | 4/1875 | Van Wagener | 85/22 |
| 1,286,551 | 12/1918 | Davis | 401/82 |
| 2,098,581 | 11/1937 | Jones | 403/289 |
| 2,108,442 | 2/1938 | Phillips | 401/82 |
| 2,289,785 | 7/1942 | Hutchison | 10/10 R |
| 2,705,643 | 4/1955 | Green | 279/96 |
| 3,044,613 | 7/1962 | Levy | 401/82 |
| 3,085,339 | 4/1963 | Wolfe | 433/4 |
| 3,135,521 | 6/1964 | Eve | 279/46 A |
| 3,250,453 | 5/1956 | Halstead | 226/127 |
| 3,252,645 | 5/1966 | Zoltai | 226/127 |
| 3,675,328 | 10/1979 | Weissman | 433/225 |
| 3,928,915 | 12/1975 | Ellman | 433/225 |
| 4,057,186 | 11/1977 | Hedger | 226/127 |
| 4,138,048 | 2/1979 | Lemmon | 226/127 |
| 4,155,162 | 5/1979 | Weissman | 433/87 |

FOREIGN PATENT DOCUMENTS 949220 of 1949 France ................................... 85/22

*Primary Examiner*—Robert Peshock
*Assistant Examiner*—Michael J. Foycik, Jr.

[57] ABSTRACT

A novel hand tool for dental use for dispensing wire, pins or rod and for manipulating the dispensed material in a dental procedure. In a preferred embodiment, the dispensed material is a strip of notched pins for cementing to tooth dentin in a retentive pin procedure.

13 Claims, 6 Drawing Figures

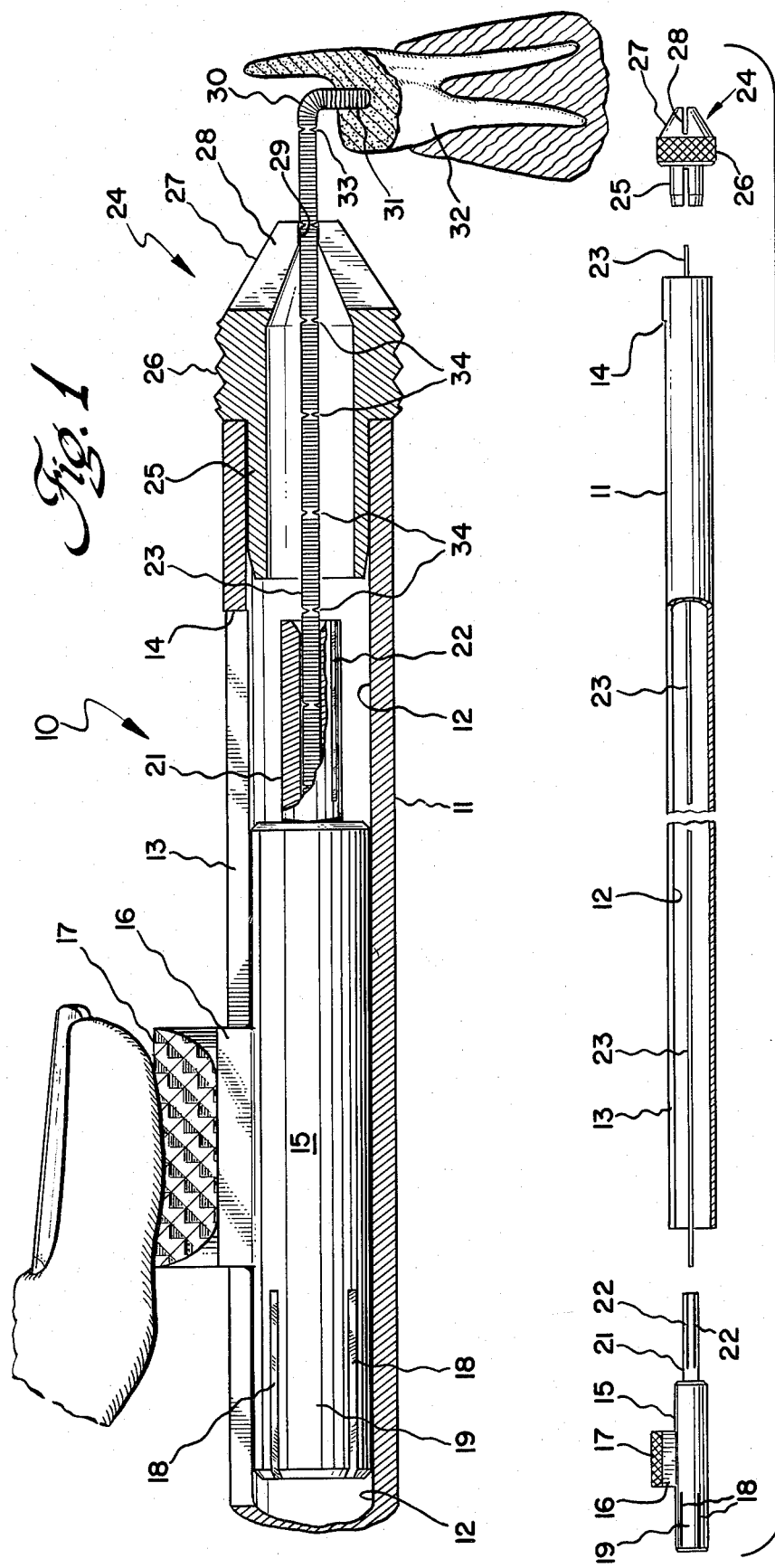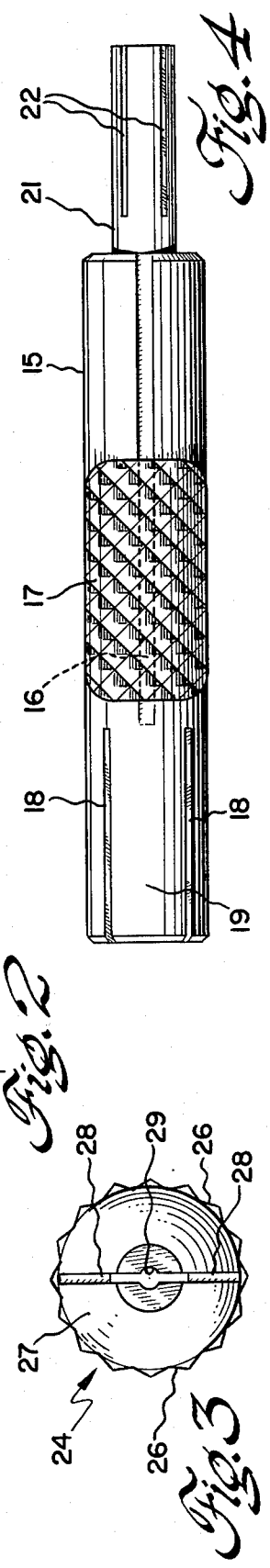

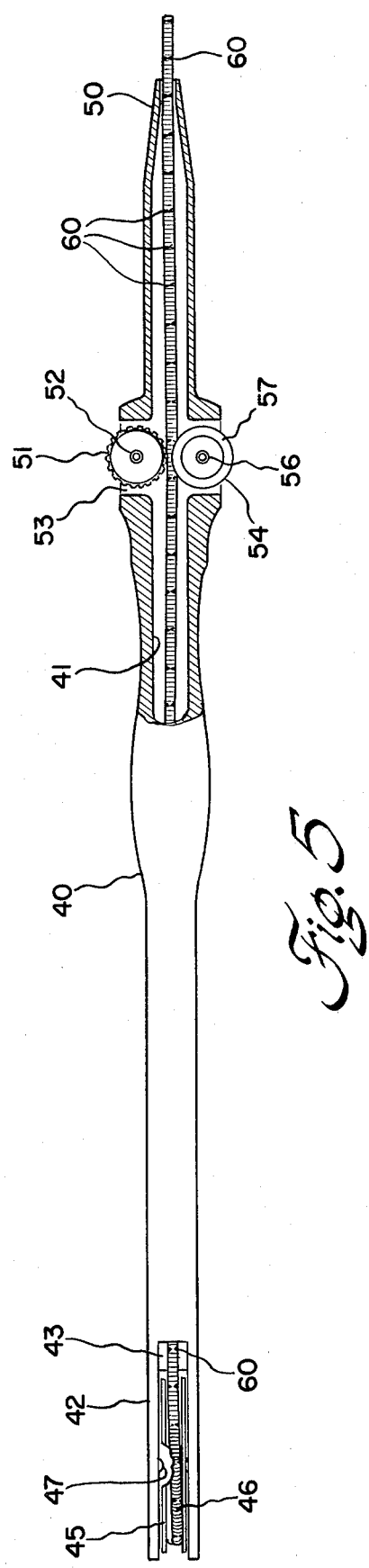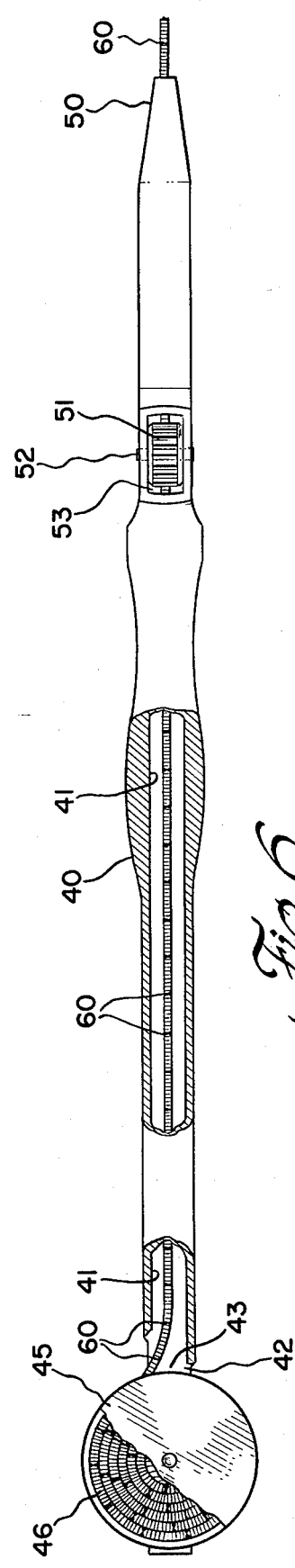

DENTAL WIRE DISPENSER AND MOUNTING TOOL

This is a continuation of application Ser. No. 61,276 filed July 27, 1979, now abandoned, which is a continuation-in-part of our copending application, Ser. No. 917,533, filed June 21, 1978 and is now abandoned.

This invention relates to wire dispensers, holders and mounting tools for use in dentistry, and in particular for tools for dispensing wire as needed by the dentist who can then apply the wire with the same tool directly to the tooth of a patient. It more specifically relates to a tool for dispensing and inserting retentive pins into a patient's tooth for anchoring with a suitable cement.

Current restorative procedures include the anchorage of retentive pins to dentin by anchor filling material, such as alloy, cement, or composite resin. Such procedures have been used for the restoration of fractured incisors, the reconstruction of coronal cores, and for many other clinical applications.

Three methods of anchorage are currently in use: the cemented, the friction-lock and the self-threading pin. The friction-lock and self-threading pins rely on the elasticity of the dentin for retention. The cemented pin is used with zinc phosphate cement or more recently an adhesive based on cyanoacrylate with its unique adhesive qualities. Other cementing mediums can also be used. Irrespective of the cement used, cementing procedure remains the same. A twist drill is used to predrill in the dentin a hole approximately 0.002 inches larger in diameter than the pins, which hole extend into the tooth to a depth of 2 to 2.5 mm. Pins may be made in a variety of alloys including stainless steel, gold, etc. They also may have many different surfaces, such as complete threading, serrations, knurling, or simply smooth. Pins are obtained from suppliers usually packaged pre-cut to 4.5 mm. in vials or in a straight wire length. In either packaging a great deal of time is wasted in the handling and selection and grasping of a pre-cut pin with pliers and to ensure that the pin is secure in the plier grooves. Several suppliers provide special grooved beak pliers with locking features so that the pin will not drop out until placed into the dentin hole and released. Then, a bending tool must be used to bend the pin to the proper contour resulting in more wasted time of the dentist. When provided in straight wire length, the rod must be measured and cut to correct size, then carried with holders and the same steps followed as above.

In U.S. Pat. No. 3,928,915, whose contents are hereby incorporated by reference, an improved pin supply is described wherein an elongated strip of pins is provided, notched at periodic intervals to provide individual pins when the strip is broken off at the notches. In this patented invention, a plurality of pins can be handled as a unit, the end pin inserted into the dentin hole and anchored therein by cement, and then the strip broken at the adjacent notch, the next free pin end inserted in another dentin hole and anchored therein, followed again by breaking of the strip at the adjacent notch, and so on, until the desired number of pins have been mounted.

But this patented procedure suffers from the drawback that a separate bending tool is still necessary to orient the pins as desired, and also that the pin strip is handled by the dentist, making it difficult to maintain sterile conditions.

An object of the present invention is to achieve increased simplicity, economy, control and safety than has heretofore been obtainable in dental pin placement procedures.

A further object of the invention is a simple tool for the handling, placement, retraction, bending and application of pins for use in a cementing technique.

Still a further object of the invention is a tool for dispensing dental wire or rod and that can also function to mount the wire or rod on a patients tooth, which tool can be used not only for inserting retentive pins, but also for inserting posts and wiring teeth in a splinting procedure.

These and other objects and advantages as will appear hereinafter are achieved, briefly speaking, with a hand tool characterized in that it comprises a handle having a hollow interior for receiving an elongated wire strip. An end of the handle is provided with a nozzle-like configuration. Means are provided on the handle for dispensing the wire strip from the handle interior through the nozzle to the outside. The nozzle is configured to enable the dentist to manipulate the protruding wire end as desired.

The invention will now be described in greater detail with reference to the accompanying drawings illustrating several exemplary embodiments of the invention, wherein:

FIG. 1 is a side, partly sectioned view showing use of a first embodiment of the tool of the invention;

FIG. 2 is an exploded view of the parts of the tool in FIG. 1 prior to assembly;

FIG. 3 is an end view of the nozzle end of the tool of FIG. 2;

FIG. 4 is a top view of the slide member of the tool of FIG. 2;

FIG. 5 is a side, partly sectioned view of a second embodiment of the tool of the invention;

FIG. 6 is a top view of the tool of FIG. 5.

FIGS. 1–4 show a first embodiment of the tool of the invention using a slide member to propel the wire forwardly. The tool, designated 10, comprises an elongated cylindrical handle 11 having a central bore 12 of uniform diameter. A slot 13 extends lengthwise along the handle side so as to extend to the central bore 12, but terminates short of the nozzle end at 14. A slide member 15 is configured to fit with a resistance fit within the bore 12, and has a tab 16 shaped to protrude through the slot 13 above the handle. The tab top surface may be knurled as shown at 17 for easier actuation by the dentist. The resistance fitting is provided by adding slits or grooves 18 to a rear hollow portion 19 of the slide member 15 so that the cylindrical portion 19 is slightly resilient and fits snugly within the handle bore 12. The forward end of the slide 15 is provided with a reduced diameter cylindrical portion 21, also hollow, and likewise provided with resilient contributing slits or grooves 22 for detachably receiving in a snug fit the end of a strip of wire 23. The wire 23 extends lengthwise within the handle bore 12. A nozzle 24 is removably mounted within the bore 12 at one end of the handle. The nozzle 24 has a rearward projecting hollow cylindrical extension 25, likewise slitted to provide a snug fit within the handle bore 12. The central portion of the nozzles is knurled as shown at 26 to facilitate grasping and handling by the dentist for manipulating the wire. The forward end of the nozzle is tapered as shown at 27 to improve visibility of the wire. It is also slotted at 28 to provide a snug fit with the wire 23 which passes through the nozzle exiting via an orifice 29 in the nozzle.

To assemble the tool, the wire 23 is inserted into the wire-receiving end 21 of the slide 15, and then that subassembly is inserted into the handle 11 from the left end, with the tab 16 engaging the handle slot 13. Then the nozzle 24 is pushed over the protruding end of the straight wire 23 and fitted into the right end of the handle 11.

The various parts of the tool can be made out of metal or plastic. A typical length would be about eight inches, which can be loaded with a length of wire capable of supplying 15–30 individual pins, obtained by breaking the wire at notches 34 located between adjacent pin lengths.

The tool can be used in several ways. In the preferred way, with the handle held in the user's hand, the slide 15 is advanced by the user's thumb until, say, one-half a pin length protrudes from the nozzle end. Then the dentist uses the tool to bend the pin (shown at 30 in FIG. 1) to a desired angle by pressing the pin end against any hard surface. Next, the wire is again advanced until the bent pin and part of the succeeding pin protrudes from the nozzle, the pin end 31 is dipped into a suitable adhesive as described in U.S. Pat. No. 3,928,915, and the adhesive-coated pin end inserted into the pre-drilled hole in a patient's tooth 32 as illustrated in FIG. 1. After the adhesive hardens, the tool is manipulated to break off the pin at the first notch 33. The procedure is now continued with succeeding pins until the desired amount of pins have been anchored to the patient's teeth. The holder above described can be used to mount retentive pins in up to 15 teeth before reloading with a new wire strip becomes necessary. As will be noted, the slide 15 can be actuated both backward as well as forward to position the protruding pin end as desired. The snug fit of the slider portion 19 will hold the slide and wire in the position desired.

Typical pin sizes are 0.023 or 0.030 inches in diameter with individual lengths of approximately 4.5 mm. While a threaded outer surface is preferred to improve retentivity, any roughened outer surface will be suitable. The surface can also be smooth if desired.

The second embodiment illustrated in FIGS. 5 and 6 uses a wheel to advance or retract the wire strip. In this embodiment, elongated handle 40 is provided having a hollow interior 41 and a bifurcated rear end 42 forming a slot 43 for receiving and supporting a spool 45 on which is coiled a supply of wire 46. The bifurcated end 42 is provided with small protuberances 47 which fit into opposite sides of the spool center to support same. Spreading of the bifurcated ends 42 allows removal and replacement of the spool 45. The handle 40 is made in one piece with a tapered forward end 50 and is configured to fit comfortably within the dentist's hand. The wire 46 passes from the spool 45 completely through the handle interior 41 and exits (at the right in FIG. 5) through an orifice at the tapered end. The wire passes with a snug fit through the forward end 50 for ready manipulation by the dentist in the same manner as the tool of FIG. 1.

Movement of the wire is effected by means of a thumb wheel 51 which is journalled via a pin 52 in a side wall of holder and within a vertical slot 53 which allows the wheel 51 to engage the top surface of the wire 46. The surface of wheel 51 may be knurled as shown to facilitate movement by the user and increase the frictional engagement with the wire. On the opposite side of the wire is journalled on idler wheel 54 via a pin 56 and is also mounted in the vertical slot 53. The idler wheel mounting is similar to that of the drive wheel 51. The idler 54 is provided with a thick resilient rim covering which has sufficient flexibility to allow the wire to be pushed through between the knurled edge of the drive wheel 51 and the resilient rim 57 of the idler yet provide enough back force so that rotation of the drive wheel 51 will cause the wire to be advanced or retracted within the handle under control of the user. If desired, the tool of FIG. 5 can also be used with a straight wire without use of the spool supply. For use in a retentive pin technique, the wire 46 can be notched at equally spaced intervals as shown at 60.

As will be apparent from the foregoing description, the tool of the invention offers the following advantages. In a retentive pin technique, the pins do not have to be individually handled. The dentist dispenses each pin as needed, to ᴄ length less than the distance between notches if so desired, inserts the pin end into the dentin hole with adhesive to anchor same, and then can use the tool to bend the pin to the desired orientation. Then, the pin is advanced to the notch (actually the tool backed off from the mounted pin), and broken off at the notch. The procedure can be repeated for as many pins as are needed. The procedure is fast, economic, and safe. Little risk exists of accidental dropping of a pin and aspiration by the patient.

The same tool mechanism can be used for inserting posts into root canals, employing a notched rod from which individual posts can be severed as needed.

The same tool mechanism can also be used for dispensing wire which can be wrapped around loose teeth by the tool for splinting purposes. In this case, the wire need not be notched as is preferably done with the strip when used for pins or posts, and the wire can be severed with a pair of wire clippers wherever desired by the dentist.

Another advantage stems from the fact that the wire need never be personally touched or handled, since the dispensed wire is manipulated by the tool handle. As a result, the tool with a supply of the wire, or replacement wire supplies, can be sterilized or supplied packaged in a sterile pack, and the sterile wire maintained in sterile condition within the handle, allowing use on different patients with reduced risk of infection.

While our invention has been described in connection with specific embodiments thereof, those skilled in the art will recognize that various modifications are possible within the principles enunciated herein and thus the present invention is not to be limited to the specific embodiments disclosed.

In the FIG. 1 embodiment, the nozzle 27 is removable. This offers the advantage that the same tool can accommodate different sized wires by simply substituting a nozzle with an orifice 29 dimensioned to fit the wire size desired. Similarly, the slide 15 can be replaced with a slide having a part 21 sized to accommodate the wire to be used.

Also, the nozzle 24 in the FIG. 1 embodiment need not be straight as illustrated. It can also be replaced by a nozzle which is bent to form an obtuse angle as illustrated by the head portions on the tool of our parent application, Ser. No. 917,533. This will allow the dentist to have completely unobstructed access to the posterior area and surface of the mouth, as well as the interior. The posterior section, labial, distal mesial and lingual angles or areas are more difficult to access, and a prebent nozzle will improve access. This feature can also be applied to the FIG. 5 embodiment.

Similarly, the nozzle end or tip of both tools can be made of flexible metal or plastic tubing, for example, corrugated metal, which will allow the dentist to bend the tip to form a desired straight or obtuse angle to improve access to the mouth area desired. The angle chosen should not be too sharp so as to impede advancement or retraction of the wire.

What is claimed is:

1. In combination with an elongated continuous strip of threaded straight dental pins of predetermined diameter notched at periodic intervals, a dental pin dispenser for dispensing and mounting said threaded pins, said dispenser comprising an elongated substantially tubular handle having a hollow interior portion for receiving the continuous strip of threaded pins and at one handle end a nozzle having an exiting orifice leading to the interior, said exiting orifice being sized and adapted to provide a snug fit with the continuous strip of pins and yet allow passage of the strip from the handle interior to the outside, said nozzle being adapted to allow a dentist holding the dispenser handle to manipulate a pin at the strip end and which pin end protrudes from the nozzle for inserting the pin end into a predrilled hole in tooth dentin and for breaking off the pin from the strip at a notch after cementing the pin in the tooth hole, said elongated length of continuous strip of threaded pins extending lengthwise within the handle interior and aligned with the nozzle orifice, and means on the handle and connected to said strip for gripping and sliding said strip from the interior through the nozzle orifice to the outside under control of the dentist.

2. The combination as claimed in claim 1, wherein the nozzle is contructed to be removably mounted at said one handle end.

3. The combination as claimed in claim 2, wherein the strip gripping and sliding means comprises a slide member constructed to be removably mounted within the handle and to frictionally engage the strip.

4. The combination as claimed in claim 1, wherein a spool is provided rotatably mounted at the opposite end of the handle, the strip being coiled on the spool and extending from the spool into said handle interior.

5. The combination as claimed in claim 1, wherein the strip-advancing means comprises a slide member, said handle interior being sized to frictionally receive a portion of the slide member and being configured to enable sliding axial movement of the slide member by the user, and means at a forward end of the slide member for detachable coupling to the strip whereby movement of the slide member advances the strip through the handle.

6. The combination as claimed in claim 5, wherein the slide member has a rear portion means enabling the slide to be snugly fitted within the handle interior to provide resisted movement of the slide.

7. The combination as claimed in claim 6, wherein both ends of the slide are provided with slits to enable friction fitting with the housing interior and with the strip, respectively.

8. The combination as claimed in claim 1, wherein the strip-advancing means comprises a wheel mounted for rotation on the handle, said wheel frictionally engaging the strip.

9. The combination as claimed in claim 8, wherein an idler wheel with a resilient rim is rotatably mounted on the handle for engaging the opposite side of the strip with the resilient rim.

10. The combination as claimed in claim 1, wherein the strip comprises at least 15 pins.

11. The restorative dental procedure for mounting a succession of threaded dental pins into plural predrilled holes in tooth dentin comprising:
   a. providing a dispensing tool having an elongated substantially tubular handle with a hollow interior portion and at one handle end a nozzle having an exiting orifice leading to the interior, said exiting orifice being sized and adapted to provide a snug fit and yet allow passage of a strip from the handle interior to the outside, said nozzle being adapted to allow a dentist holding the handle to manipulate a pin end protruding from the nozzle, an elongated strip of threaded straight dental pins notched at periodic intervals extending lengthwise within the handle interior and aligned with the nozzle orifice, and means on the handle and connected to said strip for gripping and sliding same from the interior through the nozzle orifice to the outside under control of the dentist;
   b. sliding the strip through the tool until the end pin of the strip protrudes from the nozzle;
   c. coating a tooth hole or the pin end with adhesive;
   d. manipulating the tool to insert the protruding end of the pin end into the tooth hole to anchor the pin therein by the adhesive;
   e. sliding the strip through the tool until the notch adjacent the end pin exits from and is located adjacent the tool end;
   f. following steps d. and e., manipulating the tool to break off the anchored end pin from the remainder of the strip;
   g. and repeating steps b-f until an individual dental pin has been cemented into each of the plural holes in the tooth dentin.

12. The procedure of claim 11 wherein before step c., the strip is slid until the end pin only partially protrudes from the nozzle, and next the tool is manipulated to bend the partially protruding end pin to a desired configuration.

13. The procedure of claim 12 wherein the end pin is bent by pressing the protruding end by means of the tool against a hard surface.

* * * * *